(12) United States Patent
Shalyaev et al.

(10) Patent No.: US 6,440,893 B1
(45) Date of Patent: Aug. 27, 2002

(54) METHOD AND CATALYST COMPOSITION FOR PRODUCING AROMATIC CARBONATES

(75) Inventors: Kirill Vladimirovich Shalyaev, Clifton Park; Bruce Fletcher Johnson, Scotia; Donald Wayne Whisenhunt, Jr., Niskayuna; Grigorii Lev Soloveichik, Latham, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/822,158

(22) Filed: Mar. 30, 2001

(51) Int. Cl.[7] ............................. B01J 30/28; B01J 27/26; B01J 27/24; B01J 21/02

(52) U.S. Cl. .................. 502/170; 502/171; 502/175; 502/200; 502/207; 502/349

(58) Field of Search ..................... 502/185, 399, 502/261, 170, 171, 175, 269, 207, 349

(56) References Cited

U.S. PATENT DOCUMENTS

| | | |
|---|---|---|
| 4,187,242 A | 2/1980 | Chalk |
| 5,231,210 A | 7/1993 | Joyce et al. |
| 5,239,106 A | 8/1993 | Shafer |
| 5,284,964 A | 2/1994 | Pressman et al. |
| 5,373,083 A | 12/1994 | King et al. |
| 5,380,907 A | 1/1995 | Mizukami et al. |
| 5,399,734 A | 3/1995 | King et al. |
| 5,498,789 A | 3/1996 | Takagi et al. |
| 5,502,232 A | 3/1996 | Buysch et al. |
| 5,543,547 A | 8/1996 | Iwane et al. |
| 5,726,340 A | 3/1998 | Takagi et al. |
| 5,760,272 A | 6/1998 | Pressman et al. |
| 5,821,377 A | 10/1998 | Buysch et al. |
| 5,856,554 A | 1/1999 | Buysch et al. |
| 6,197,991 B1 | 3/2001 | Spivack et al. |

FOREIGN PATENT DOCUMENTS

| | | |
|---|---|---|
| DE | 736325 | 3/1996 |
| JP | 10158221 | 6/1980 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | 10/1997 |
| JP | 97-278716 | 10/1997 |

*Primary Examiner*—Johann Richter
*Assistant Examiner*—Ebenezer Sackey
(74) *Attorney, Agent, or Firm*—Noreen C. Johnson; Christian G. Cabou

(57) ABSTRACT

A method and catalyst composition for economically producing aromatic carbonates from aromatic hydroxy compounds is disclosed. The present invention provides a method for carbonylating aromatic hydroxy compounds, comprising the step of contacting at least one aromatic hydroxy compound with oxygen and carbon monoxide in the presence of a halide-free carbonylation catalyst composition comprising an effective amount of at least one Group 8, 9, or 10 metal source, an effective amount of a first inorganic co-catalyst comprising at least one Group 14 metal source, an effective amount of a salt co-catalyst, and optionally an effective amount of a second inorganic co-catalyst selected from the group consisting of a Group 4 metal source, a Group 7 metal source, a Group 11 metal source, and a lanthanide element source, and optionally an effective amount of a base. A significant advantage of the present method and catalyst compositions is that no halide is present or required in the reaction mixture for catalytic activity.

36 Claims, No Drawings

US 6,440,893 B1

METHOD AND CATALYST COMPOSITION FOR PRODUCING AROMATIC CARBONATES

BACKGROUND OF THE INVENTION

The present invention is directed to a catalyst composition and method for producing aromatic carbonates through the carbonylation of aromatic hydroxy compounds.

Aromatic carbonates find utility, inter alia, as intermediates in the preparation of polycarbonates. For example, a popular method of polycarbonate preparation is the melt transesterification of aromatic carbonates with bisphenols. Various methods for preparing aromatic carbonates have been previously described in the literature and utilized by industry. A method that has enjoyed substantial popularity in the literature involves the direct carbonylation of aromatic hydroxy compounds with carbon monoxide and oxygen catalyzed by at least one Group 8, 9 or 10 metal source. Further refinements to the carbonylation catalyst composition include the identification of co-catalysts.

The utility of the carbonylation process is strongly dependent on the number of moles of desired aromatic carbonate produced per mole of Group 8, 9, or 10 metal utilized (i.e. "catalyst turnover number or 'TON'"). Consequently, much work has been directed to the identification of efficacious catalyst compositions that increase the catalyst turnover number.

Carbonylation catalyst literature lauds the effectiveness of halide salts, particularly bromide salts, in catalyst compositions for improving catalyst TON's. While it is true that catalyst compositions that contain halide salts have historically exhibited high activity, there are drawbacks to using halide in a carbonylation reaction. For example, when used to carbonylate phenol, bromide anions are consumed in the process, forming undesirable brominated byproducts, such as 2- and 4-bromophenols and bromodiphenylcarbonate.

It would be desirable to identify catalyst compositions that would minimize consumption of components or perhaps that would omit components such as halide. It would also be desirable to increase selectivity toward the desired carbonate product and minimizing formation of undesirable halogenated byproducts.

As the demand for high performance plastics has continued to grow, new and improved methods of providing product are needed to supply the market. Consequently, a long felt, yet unsatisfied need exists for new and improved methods and catalyst compositions for producing aromatic carbonates and the like.

SUMMARY OF THE INVENTION

Accordingly, the present invention is directed to a method and catalyst composition for producing aromatic carbonates. In one embodiment, the present invention provides a method for carbonylating aromatic hydroxy compounds, comprising the step of contacting at least one aromatic hydroxy compound with oxygen and carbon monoxide in the presence of a carbonylation catalyst composition comprising an effective amount of at least one Group 8, 9, or 10 metal source, an effective amount of at least one inorganic co-catalyst comprising a Group 14 metal source, and an effective amount of at least one salt co-catalyst, wherein the carbonylation catalyst composition is free of a halide source.

DETAILED DESCRIPTION OF PREFERRED EMBODIMENTS

The present invention is directed to a carbonylation method and catalyst composition for producing aromatic carbonates. The constituents of the carbonylation catalyst composition are defined as "components" irrespective of whether a reaction between the constituents occurs before or during the carbonylation reaction. Thus, the catalyst composition typically includes the components and any reaction products thereof. In one embodiment, the method includes the step of contacting at least one aromatic hydroxy compound with oxygen and carbon monoxide in the presence of a carbonylation catalyst composition comprising an effective amount of at least one Group 8, 9, or 10 metal source, an effective amount of an inorganic co-catalyst comprising at least one Group 14 element source, and an effective amount of at least one salt co-catalyst, wherein the carbonylation catalyst composition is free of a halide source. Unless otherwise noted, the term "effective amount," as used herein, includes that amount of a substance capable of yielding the desired aromatic carbonate, or also includes that amount of a substance that increases the selectivity of any one of the starting reagents (e.g. oxygen, carbon monoxide, and aromatic hydroxy compound) towards the desired aromatic carbonate. In another embodiment, the method includes the step of contacting at least one aromatic hydroxy compound with oxygen and carbon monoxide in the presence of a carbonylation catalyst composition that comprises an effective amount of at least one Group 8, 9, or 10 metal source, an effective amount of at least one first inorganic co-catalyst comprising at least one Group 14 element source, an effective amount of at least one second inorganic co-catalyst selected from the group consisting of a Group 4 metal source, a Group 7 metal source, a Group 11 metal source, and a lanthanide element source; and an effective amount of at least one salt co-catalyst, wherein the catalyst composition is free of a halide source. In yet another embodiment, the method includes the step of contacting at least one aromatic hydroxy compound with oxygen and carbon monoxide in the presence of a carbonylation catalyst composition that comprises an effective amount of at least one Group 8, 9, or 10 metal source, an effective amount of at least one first inorganic co-catalyst comprising at least one Group 14 element source, an effective amount of at least one second inorganic co-catalyst selected from the group consisting of Group 4 metal sources, and lanthanide element sources; an effective amount of at least one salt co-catalyst, and an effective amount of at least one base, wherein the catalyst composition is free of a halide source Any aromatic hydroxy compound, which is convertible to a carbonate ester, is suitable in the present invention. For example, suitable aromatic hydroxy compounds include, but are not limited to, monocyclic, polycyclic or fused polycyclic aromatic monohydroxy or polyhydroxy compounds having from about 6 to about 30, and preferably from about 6 to about 15 carbon atoms. Illustrative examples include but are not limited to phenol, alkylphenols, alkoxyphenols, biphenols, bisphenols, and salicylic acid derivates such as methyl salicylate.

The carbonylation catalyst composition contains at least one catalyst component selected from Group 8, 9 or 10 metal sources. Typical Group 8, 9 or 10 metal sources include ruthenium sources, rhodium sources, palladium sources, osmium sources, iridium sources, platinum sources, and mixtures thereof. The quantity of the Group 8, 9, or 10 metal source is not limited in the process of the present invention. The amount employed should be about 1 gram of Group 8, 9, or 10 metal per 100 grams to 1,000,000 grams of aromatic hydroxy compound (i.e. about 1 part per million (ppm) to about 10,000 ppm of Group 8, 9, or 10 metal). For example, about 1 ppm to about 1000 ppm of Group 8, 9, or 10 metal is suitable. In one embodiment of the present invention about 1 ppm to about 30 ppm of Group 8, 9, or 10 metal is used. A typical Group 8, 9, or 10 metal source is a palladium source. The palladium source used is typically in the Pd (II) oxidation state at the beginning of the reaction. Alternatively, a palladium compound in either the Pd(O) or Pd(IV) oxidation states can be used. As used herein, the term "compound" includes inorganic, coordination and organometallic complex compounds. The compounds are typically neutral, cationic, or anionic, depending on the charges carried by the central atom and the coordinated ligands. Other common names for these compounds include complex ions (if electrically charged), Werner complexes, and coordination complexes. A Group 8, 9, or 10 metal source can be employed in a homogeneous form that is substantially soluble in the reaction media or in a heterogeneous form which is substantially insoluble in the reaction media, including supported or polymer bound species. Examples of suitable palladium sources include, but are not limited to, palladium sponge, palladium black, palladium deposited on carbon, palladium deposited on alumina, palladium deposited on silica, palladium sulfates, palladium nitrates, palladium carboxylates, palladium oxides, palladium acetates, palladium salts of β-diketones, palladium salts of β-ketoesters, and palladium compounds containing any of the following ligands: carbon monoxide, amine, nitrite, nitrile, isonitrile, phosphine, phosphite, phosphate, alkoxide, alkyl, aryl, silyl or olefin. In one embodiment palladium(II) acetate is used. In another embodiment palladium(II) 2,4-pentanedionate is used.

The carbonylation catalyst composition in the present invention further contains an effective amount of at least one first inorganic co-catalyst (IOCC) comprising at least one Group 14 element source. As used herein, the term "inorganic co-catalyst" includes any catalyst component that contains a metal element, which is present in the catalyst composition in addition to the Group 8, 9 or 10 metal source. The Group 14 element source is at least one selected from the group consisting of silicon, germanium, tin, and lead. In an alternative embodiment of the invention, a second IOCC selected from the group consisting of Group 4 metal sources, and lanthanide element sources, is also present in the catalyst composition. The Group 4 metal source is at least one selected from the group consisting of zirconium, hafnium, and titanium. The Group 7 metal source is at least one selected from the group consisting of rhenium and manganese. The Group 11 metal source is at least one selected from the group consisting of silver, gold and copper. The lanthanide element source is at least one selected from the group consisting of praseodymium, neodymium, promethium, samarium, europium, gadolinium, terbium, dysprosium, holmium, erbium, thulium, ytterbium, and lutetium and preferably cerium. Suitable forms of Group 14, Group 4, Group 7, Group 11, and lanthanide IOCC's include, but are not limited to, elemental metals, metal salts, metal compounds in stable oxidation states, and precursors thereof which form catalytically active metal species under the reaction conditions. The compounds are typically neutral, cationic, or anionic, depending on the charges carried by the central atom and the coordinated ligands. Illustrative examples of Group 14, Group 4, Group 7, Group 11, and lanthanide IOCC's include but are not limited to oxides, carboxylates, acetates, salts of β-diketones, salts of β-ketoesters, nitrates, and compounds containing any of the following ligands: carbon monoxide, amine, nitrite, nitrite, isonitrile, cyanide, phosphine, phosphite, phosphate, alkoxide, alkyl, aryl, silyl or olefin. The IOCC's are typically initially soluble in the reaction mixture, and typically remain soluble or become at least partially insoluble during the course of the reaction, or they are typically initially insoluble in the reaction mixture, and remain either insoluble or become at least partially soluble during the course of the reaction. Alternatively, the IOCC's are typically supported or polymer-bound with a variety of support media, including but not limited to carbon, alumina, silica, and zeolites.

In addition to the Group 8, 9, or 10 metal catalyst, at least one Group 14 element is present as a first IOCC in the carbonylation catalyst composition. In one embodiment the Group 14 element is lead. Illustrative examples of suitable lead sources include, but are not limited to, lead oxides such as lead(II) oxide, tri-lead tetraoxide, and lead(IV) oxide, lead carboxylates such as lead acetate and lead proprionate, inorganic lead salts such as lead nitrate and lead sulfate, alkoxy and aryloxy lead compounds such as lead methoxide and lead phenoxide, lead β-diketone compounds such as lead(II) 2,4-pentanedionate, organometallic lead compounds having at least one lead-carbon bond, e.g., alkyl lead compounds such as tetraethyllead(IV), and lead compounds containing any of the following ligands: carbon monoxide, amine, nitrite, nitrite, isonitrile, cyanide, phosphine, phosphite, phosphate, alkoxide, alkyl, aryl, silyl or olefin. In one embodiment, the lead source is lead(II) oxide. In another embodiment the lead source is tetraethyllead(IV). Mixtures of lead compounds are also suitable.

In an alternative embodiment, in addition to the first IOCC comprising a Group 14 metal source, a second IOCC is typically present in the carbonylation catalyst composition. The second IOCC is at least one member selected from the group consisting of a Group 4 metal source, a Group 7 metal source, a Group 11 metal source, and a lanthanide element source.

An example of a Group 4 metal source is a titanium source. Illustrative examples of titanium sources include, but are not limited to, titanyl oxides, titanium alkoxides, titanium aryloxides, titanium nitrates, titanium carboxylates, and titanium sulfates. Additional examples of titanium sources include titanium compounds containing any one of the following ligands: carbon monoxide, amine, nitrite, nitrate nitrite, isonitrile, cyanide, phosphine, phosphite, phosphate, alkoxide, alkyl, aryl, silyl, olefin, β-diketone, or β-ketoester. In one embodiment the titanium source is titanium(IV) oxide 2,4-pentanedionate. Mixtures of titanium sources are also suitable.

An example of a Group 7 metal source is a manganese source. Illustrative examples of manganese sources include but are not limited to manganese nitrates, manganese carboxylates, manganese sulfate, and manganese compounds containing any one of the following ligands: carbon monoxide, amine, nitrite, nitrite, isonitrile, cyanide, phosphine, phosphite, phosphate, alkoxide, alkyl, aryl, silyl, olefin, β-diketone, or β-ketoester. In one embodiment the manganese source is manganese (III) 2,4-pentanedionate. Mixtures of manganese sources are also suitable.

An example of a Group 11 metal source is a copper source. Examples of copper sources include but are not limited to copper oxides, copper alkoxides, copper aryloxides, copper nitrate, copper carboxylates, copper sulfate, and copper compounds containing any one of the following ligands: carbon monoxide, amine, nitrite, nitrite, isonitrile, cyanide, phosphine, phosphite, phosphate, alkoxide, alkyl, aryl, silyl, olefin, β-diketone, or β-ketoester. In one embodiment the copper source is copper(II) 2,4-pentanedionate. Mixtures of copper sources are also suitable.

An example of a lanthanide element source is a cerium source. Illustrative examples of cerium sources include, but are not limited to, cerium oxides, cerium alkoxides, cerium aryloxides, cerium nitrate, cerium carboxylates, cerium sulfate, and cerium compounds containing any one of the following ligands: carbon monoxide, amine, nitrite, nitrite, isonitrile, cyanide, phosphine, phosphite, phosphate, alkoxide, alkyl, aryl, silyl, olefin, β-diketone, or β-ketoester. In one embodiment the cerium source is cerium(III) acetate. In another embodiment the cerium source is cerium(III) 2,4-pentanedionate. Mixtures of lanthanides sources, including but not limited to, cerium sources are also suitable.

In one embodiment of the present invention, in addition to the inorganic components at least one organic co-catalyst salt is also present. As used herein, the term "organic co-catalyst salt" includes any catalyst component which is present in the catalyst composition, in addition to the Group 8, 9 or 10 catalyst and any IOCC source, which comprises an anion selected from the group consisting of acetate, carboxylate, benzoate, sulfate, nitrate, tetraarylborate, alkylsulfonate, arylsulfonates, or cyanide.

Typical organic co-catalyst salts contain a cation selected from the group consisting of an alkali metal cation, an alkaline-earth metal cation, guanidinium, or an onium cation. Examples of onium cations include ammonium cations, phosphonium cations, and sulfonium cations. In various embodiments the organic co-catalyst salts used include sodium carboxylates (e.g. sodium acetate), tetraalkylammonium carboxylates (e.g. tetrabutylammonium benzoate), tetraalkylammonium sulfates (e.g. tetrabutylammonium sulfate), tetraalkylammonium nitrates (e.g. tetrabutylammonium nitrate) tetraalkylammonium tetraarylborates (e.g. tetrabutylammonium tetraphenylborate), tetraalkylammonium sulfonates, (e.g. tetraethylammonium para-tolylsulfonate), and tetraalkylammonium cyanides (e.g. tetraethylammonium cyanide).

In yet another alternative embodiment, at least one base is typically present in carbonylation catalyst composition of the present invention. Suitable bases include, but are not limited to, alkali metal or alkaline-earth metal, guanidinium, or onium salts of basic oxides, hydroxides, mono or polyalkoxides with linear or branched alkyl chains having from about 1 to about 30 carbon atoms, aryloxides including monocyclic, polycyclic or fused polycyclic aromatic monohydroxy or polyhydroxy compounds having from about 6 to about 30, and preferably from about 6 to about 15 carbon atoms. Typical onium cations contain organic residues, which typically include $C_{1-20}$ alkyl, $C_{6-10}$ aryl, or alkyl-aryl combinations thereof. A second suitable class of bases includes tertiary amines with organic residues which contain alkyl residues having from about 1 to about 20 carbon atoms, aryl residues having from about 6 to about 30, and preferably from about 6 to about 15 carbon atoms, or alkyl-aryl combinations thereof. Typical bases include, but are not limited to, sodium hydroxide, lithium hydroxide, potassium hydroxide, tetraalkylammonium hydroxides (e.g. tetramethylammonium hydroxides, tetraethylammonium hydroxide, methyltributylammonium hydroxide and tetrabutylammonium hydroxide) sodium phenoxide, lithium phenoxide, potassium phenoxide, and tetraalkylammonium phenoxides (e.g. tetramethylammonium phenoxide, tetraethylammonium phenoxide, methyltributylammonium phenoxide and tetrabutylammonium phenoxide).

Typically, the first IOCC, comprising at least one Group 14 metal source, is present in the amount of about 0.1 mole to about 150 moles of Group 14 metal source per mole of a Group 8, 9, or 10 catalyst. In one embodiment between about 1 mole and about 100 moles of Group 14 IOCC per mole of Group 8, 9 or 10 catalyst is used. In another alternative embodiment between about 10 moles and about 70 moles of Group 14 IOCC per mole of Group 8, 9 or 10 catalyst is used. For example, when the Group 8, 9, or 10 catalyst is palladium the molar ratio of lead relative to palladium at the initiation of the reaction is typically between about 10 moles and about 70 moles per mole of palladium.

In an embodiment which contains a second IOCC, the molar ratio of the second IOCC relative to the Group 8, 9, or 10 catalyst present in the carbonylation catalyst composition at the initiation of the reaction is typically between about 0.1 mole and about 100 moles of second IOCC per mole of Group 8, 9, or 10 catalyst. In one embodiment the ratio of a second IOCC relative to the Group 8, 9, or 10 catalyst at the initiation of the reaction is between about 1 mole and about 20 moles per mole of Group 8, 9 or 10 catalyst. For example, when the Group 8, 9, or 10 catalyst is palladium, the molar ratio of the second IOCC (e.g., a titanium source, a manganese source, a copper source, or a cerium source) relative to palladium at the initiation of the reaction is typically between about 1 mole and about 100 moles per mole of palladium.

The molar ratio of the salt co-catalyst relative to Group 8, 9, or 10 catalyst present in the carbonylation catalyst composition at the initiation of the reaction is between about 0.1 mole and about 10000 moles per mole of Group 8, 9, or 10 catalyst. In one embodiment the molar ratio of the salt co-catalyst relative to Group 8, 9, or 10 catalyst is between about 1 mole and about 1000 moles. For example, when the Group 8, 9 or 10 catalyst is palladium, the molar ratio of the salt co-catalyst relative to palladium at the initiation of the reaction is typically between about 1 mole and about 600 moles per mole of palladium.

The molar ratio of the base relative to the Group 8, 9, or 10 catalyst at the initiation of the reaction is typically between about 0.1 mole and about 1000 moles of base per mole of the Group 8, 9, or 10 catalyst. In one embodiment, the molar ratio of the base relative to the Group 8, 9, or 10 catalyst is between about 1 mole and about 600 moles per mole of Group 8, 9, or 10 catalyst. For example, when the Group 8, 9 or 10 catalyst is palladium the molar ratio of the base to palladium is typically between about 1 mole and about 400 moles per mole of palladium.

The carbonylation method can be carried out in a variety of reactor systems including, but not limited to, stirred vessels, autoclaves and bubble columns, each of which is capable of being operated under batch-liquid/batch-gas reactor conditions (i.e. batch/batch), batch-liquid/continuous-gas reactor conditions (i.e. batch/flow or semi-continuous), or continuous-liquid/continuous-gas reactor conditions (i.e.flow/flow). In one embodiment two or more reactors are typically employed in a cascade. In one embodiment about 2 to about 15 reactors are used. When a reactor cascade is used instead of an individual reactor, the separate gas addition preferably proceeds in such a way that the optimal gas concentrations are ensured in each of the reactors. Due in part to the low solubility of carbon monoxide and oxygen in organic aromatic hydroxy compounds, such as phenol, it is preferable that each reactor vessel be pressurized. A total pressure in the range up to about 35 Megapascals (MPa) is used. In one embodiment the reaction pressure is between about 0.5 MPa and about 14 MPa.

The reaction gases are typically reagent grade purity, and special care must be taken to ensure that no catalyst composition poisons are present as impurities in the gas sources. In one embodiment the carbon monoxide and oxygen are introduced independently of each other into the reactor vessel. In an alternative embodiment the carbon monoxide and oxygen are introduced into the reactor vessel as a single premixed gas mixture comprising carbon monoxide and oxygen. The composition of the reaction gases comprising carbon monoxide and oxygen can be varied in broad concentration ranges. For example the volume percent oxygen in the gas mixtures can be up to about 0.1 volume % to about 20 volume %. In one embodiment the volume % of oxygen in the gas mixture is between about 1% and about 9%. Gas sparging or mixing can be used to aid the reaction. Additional inert gases, such as nitrogen, helium, neon, argon, krypton, xenon, or any other gas which has no negative effect on the carbonylation reaction can be added to the reactor vessel in order to dilute the carbon monoxide and oxygen gas mixture. For example, air is an acceptable substitute for pure oxygen. The concentration of inert gas in the reaction gas is typically up to about 60 volume %. In one embodiment the volume % of inert gas is about 0% to about 20% of the total gas volume.

Typical reaction temperatures are between about 50° C. and about 150° C. In one embodiment the reaction temperature is between about 90° C. and about 110° C. Provisions are typically made for including a drying agent or a drying process step in the overall reaction method. Higher catalyst turnover numbers are typically obtained if water is removed from the reaction mixture during the reaction.

The following examples are included to provide additional guidance to those skilled in the art in practicing the claimed invention. The examples provided are merely representative of the work that contributes to the teaching of the present application. Accordingly, the following examples are not intended to limit the invention, as defined in the appended claims, in any manner.

In the following examples, the aromatic carbonate produced is diphenyl carbonate (DPC) and the Group 8, 9, or 10 metal utilized is palladium. For convenience, the number of moles of DPC produced per mole of palladium charged to a reaction is referred to as the palladium turnover number (Pd TON), and is used as an activity metric in the following examples.

EXAMPLES 1–13

Carbonylation reactions were carried out in glass reaction vessels containing about 15 ppm to about 25 ppm of palladium(II) 2,4-pentanedionate in phenol, IOCC combinations in equivalents versus palladium, various salt co-catalyst components in equivalents versus palladium, and sodium hydroxide in equivalents versus palladium. Titanium (Ti) was added as titanium(IV) oxide 2,4-pentanedionate, manganese (Mn) was added as manganese(III) 2,4-pentanedionate, copper (Cu) was added as copper(II) 2,4-pentanedionate, and cerium (Ce) was added as cerrium(III) 2,4-pentanedionate. The components were heated to 100° C. for 3 hours in an atomosphere of about 6% to about 9% oxygen in carbon monoxide at about 11 megapascals. Amounts are in parts per million (ppm) or equivalents (eq); TBA-Benzoate is tetrabutylammonium benzoate; NaOAc is sodium acetate; TBA-SO$_4$ is tetrabutylammonium sulfate; TBA-NO$_3$ is tetrabutylammonium nitrate; TBA-BPh4 is tetrabutylammonium tetraphenylborate; TEA-tolSO$_3$ is tetraethylammonium para-tolylsulfonate; and TEA-SCN is tetraethylammonium cyanide. Average results of multiple runs are given in Tables 1–5.

TABLE 1

| Example | Pd (ppm) | PbO eq. vs. Pd | salt/ eq. vs. Pd | Pd TON |
|---|---|---|---|---|
| 1 | 25 | 50 | NaOAc/ 400 | 479 |
| 2 | 25 | 50 | TBA-benzoate/ 400 | 872 |
| 3 | 25 | 50 | TBA-SO$_4$/ 50 | 426 |
| 4 | 25 | 50 | TBA-NO$_3$/ 400 | 62 |
| 5 | 25 | 50 | TBA-BPh$_4$/ 400 | 48 |
| 6 | 25 | 50 | TEA-tolSO$_3$/ 50 | 79 |
| 7 | 25 | 50 | TEA-CN/ 50 | 84 |

TABLE 2

| Example | Pd (ppm) | PbO eq. vs. Pd | salt/ eq. vs. Pd | NaOH Eq. vs Pd | Pd TON |
|---|---|---|---|---|---|
| 8 | 25 | 50 | NaOAc/ 400 | 200 | 202 |
| 9 | 25 | 50 | TBA-benzoate/ 400 | 200 | 1028 |

TABLE 3

| Example | Pd (ppm) | PbO eq. vs. Pd | Ti eq. vs. Pd | salt/ eq. vs. Pd | Pd TON |
|---|---|---|---|---|---|
| 10 | 25 | 50 | 6 | NaOAc/ 400 | 273 |
| 11 | 25 | 50 | 6 | TBA-benzoate/ 400 | 791 |

TABLE 4

| Example | Pd (ppm) | PbO eq. vs. Pd | Ce eq. vs. Pd | salt/ eq. vs. Pd | Pd TON |
|---|---|---|---|---|---|
| 12 | 25 | 50 | 6 | NaOAc/ 400 | 258 |
| 13 | 25 | 50 | 6 | TBA-benzoate/ 400 | 1049 |

TABLE 5

| Example | Pd (ppm) | PbO eq. vs. Pd | $2^{nd}$ IOCC | $2^{nd}$ IOCC eq. vs. Pd | TMAOH eq. vs. Pd | salt/ eq. vs. Pd | Pd TON |
|---|---|---|---|---|---|---|---|
| 14 | 15 | 100 | Ti | 18 | 400 | TBA-$NO_3$/ 500 | 1679 |
| 15 | 15 | 100 | Ti | 18 | 400 | TBA-benzoate/500 | 1372 |
| 16 | 15 | 100 | Ti | 18 | 400 | TEA-tol$SO_3$/500 | 1499 |
| 17 | 15 | 100 | Ce | 12 | 400 | TBA-benzoate/500 | 1767 |
| 18 | 15 | 100 | Ce | 12 | 400 | TEA-tol$SO_3$/500 | 2027 |
| 19 | 15 | 100 | Cu | 12 | 200 | TBA-benzoate/500 | 571 |
| 20 | 15 | 100 | Cu | 12 | 200 | TBA-$SO_4$/ 500 | 809 |
| 21 | 15 | 100 | Mn | 12 | 400 | TBA-$NO_3$/ 500 | 959 |
| 22 | 15 | 100 | Mn | 12 | 400 | TBA-benzoate/500 | 1349 |
| 23 | 15 | 100 | Mn | 12 | 400 | TEA-tol$SO_3$/500 | 1525 |

It will be understood that each of the elements described above, or two or more together, typically also find utility in applications differing from the types described herein. While the invention has been illustrated and described as embodied in a method and catalyst composition for producing aromatic carbonates, it is not intended to be limited to the details shown, since various modifications and substitutions can be made without departing in any way from the spirit of the present invention. For example, additional effective IOCC compounds can be added to the reaction. As such, further modifications and equivalents of the invention herein disclosed typically occur to persons skilled in the art using no more than routine experimentation, and all such modifications and equivalents are believed to be within the spirit and scope of the invention as defined by the following claims.

What is claimed is:

1. A carbonylation catalyst composition comprising the following and any reaction products thereof:
   an effective amount of at least one Group 8, 9, or 10 metal source;
   an effective amount of at least one inorganic co-catalyst comprising a Group 14 element source; and
   an effective amount of at least one salt co-catalyst with an anion selected from the group consisting of carboxylate, benzoate, acetate, sulfate, nitrate, arylborate, alkylsulfonate, arylsulfonate, and cyanide; wherein the carbonylation catalyst composition is free of a halide source.

2. The carbonylation catalyst composition of claim 1, wherein the Group 8, 9, or 10 metal source is a palladium source.

3. The carbonylation catalyst composition of claim 2, wherein the palladium source is palladium(II) 2,4-pentanedionate.

4. The carbonylation catalyst composition of claim 1, wherein the Group 14 inorganic co-catalyst is a lead source.

5. The carbonylation catalyst composition of claim 4, wherein the lead source is one member selected from the group consisting of lead(II) oxide, tetraethyllead(IV), and lead(II) phenoxide.

6. The carbonylation catalyst composition of claim 1, wherein the salt co-catalyst contains a cation selected from the group consisting of alkali metal cation, alkaline-earth metal cation, guanidinium, and onium cation.

7. The carbonylation catalyst composition of claim 6, wherein the salt co-catalyst is at least one member selected from the group consisting of tetraalkylammonium or alkali metal carboxylates, tetraalkylammonium sulfates, tetraalkylammonium nitrates, tetraarylammonium tetrarylborates, tetraalkylammonium sulfonates, and tetraalkylammonium cyanides.

8. The carbonylation catalyst composition of claim 7, wherein the salt co-catalyst is at least one member selected from the group consisting of sodium acetate, tetrabutylammonium benzoate, tetrabutylammonium sulfate, tetrabutylammonium nitrate, tetrabutylammonium tetraphenylborate, tetraethylammonium para-tolylsulfonate, and tetraethylammonium cyanide.

9. The carbonylation catalyst composition of claim 1, further comprising an effective amount of at least one base.

10. The carbonylation catalyst composition of claim 9, wherein the base is at least one member selected from the group consisting of basic oxides, hydroxides, alkoxides, aryloxides, and amines.

11. The carbonylation catalyst composition of claim 10, wherein the base comprises at least one member selected from the group consisting of alkali metal hydroxides and alkaline-earth metal hydroxides.

12. The carbonylation catalyst composition of claim 11, wherein the base is sodium hydroxide.

13. The carbonylation catalyst composition of claim 10, wherein the base comprises at least one member selected from the group consisting of onium hydroxide and guanidinium hydroxide.

14. The carbonylation catalyst composition of claim 13, wherein the base is a tetraalkylammonium hydroxide.

15. The carbonylation catalyst composition of claim 14, wherein the base is tetramethylammonium hydroxide.

16. A carbonylation catalyst composition comprising the following and any reaction products thereof:
    an effective amount of palladium(II) 2,4-pentanedionate;
    an effective amount of lead(II) oxide; and
    an effective amount of at least one member selected from the group consisting of sodium acetate, tetrabutylammonium benzoate, tetrabutylammonium sulfate, tetrabutylammonium nitrate, tetrabutylammonium tetraphenylborate, tetraethylammonium para-tolylsulfonate, and tetraethylammonium cyanide;
wherein the carbonylation catalyst composition is free of a halide source.

17. A carbonylation catalyst composition comprising the following and any reaction products thereof:
    an effective amount of palladium(II) 2,4-pentanedionate;
    an effective amount of lead(II) oxide;
    an effective amount of at least one compound selected from the group consisting of sodium acetate, tetrabutylammonium benzoate, tetrabutylammonium sulfate, tetrabutylammonium nitrate, tetrabutylammonium tetraphenylborate, tetraethylammonium para-tolylsulfonate, and tetraethylammonium cyanide; and
    an effective amount of sodium hydroxide;
wherein the carbonylation catalyst composition is free of a halide source.

18. A carbonylation catalyst composition comprising the following and any reaction products thereof:
    an effective amount of at least one Group 8, 9, or 10 metal source;
    an effective amount of a first inorganic co-catalyst comprising at least one Group 14 element source;
    an effective amount of at least one second inorganic co-catalyst selected from the group consisting of a Group 4 metal source, a Group 7 metal source, a Group 11 metal source, and a lanthanide element source; and
    an effective amount of at least one salt co-catalyst with an anion selected from the group consisting of carboxylate, benzoate, acetate, sulfate, nitrate, arylborate, alkylsulfonate, arylsulfonate, and cyanide;
wherein the carbonylation catalyst composition is free of a halide source.

19. The carbonylation catalyst composition of claim 18, wherein the Group 8, 9, or 10 metal source is a palladium source.

20. The carbonylation catalyst composition of claim 19, wherein the palladium source is palladium(II) 2,4-pentanedionate.

21. The carbonylation catalyst composition of claim 18, wherein the first inorganic co-catalyst is a lead source.

22. The carbonylation catalyst composition of claim 21, wherein the lead source is one member selected from the group consisting of lead(II) oxide, tetraethyllead(IV), and lead(II) phenoxide.

23. The carbonylation catalyst composition of claim 18, wherein the second inorganic co-catalyst is at least one member selected from the group consisting of a titanium source, a manganese source, a copper source, and a lanthanide source.

24. The carbonylation catalyst composition of claim 23, wherein the second inorganic co-catalyst is at least one member selected from the group consisting of titanium(IV) oxide 2,4-pentanedionate, manganese(III) 2,4-pentanedionate, copper(II) 2,4-pentanedionate, and cerium (III) 2,4-pentanedionate.

25. The carbonylation catalyst composition of claim 18, wherein the salt co-catalyst contains a cation selected from the group consisting of an alkali metal cation, alkaline-earth metal cation, guanidinium cation, and an onium cation.

26. The carbonylation catalyst composition of claim 25, wherein the salt co-catalyst is at least one member selected from the group consisting of tetraalkylammonium or alkali metal carboxylates, tetraalkylammonium sulfates, tetraalkylammonium nitrates, tetraalkylammonium tetraarylborates, tetraalkylammonium sulfonates, and tetraalkylammonium cyanides.

27. The carbonylation catalyst composition of claim 26, wherein the salt co-catalyst is at least one member selected from the group consisting of sodium acetate, tetrabutylammonium benzoate, tetrabutylammonium sulfate, tetrabutylammonium nitrate, tetrabutylammonium tetraphenylborate, tetraethylammonium para-tolylsulfonate, and tetraethylammonium cyanide.

28. The carbonylation catalyst composition of claim 18, further comprising a base.

29. The carbonylation catalyst composition of claim 28, wherein the base is at least one member selected from the group consisting of basic oxides, hydroxides, alkoxides, aryloxides, and amines.

30. The carbonylation catalyst composition of claim 29, wherein the base is one member selected from the group consisting of hydroxides and alkaline-earth metal hydroxide.

31. The carbonylation catalyst composition of claim 30, wherein the base is sodium hydroxide.

32. The carbonylation catalyst composition of claim 29, wherein the base comprises at least one member selected from the group consisting of onium hydroxides and guanidinium hydroxides.

33. The carbonylation catalyst composition of claim 32, wherein the base is a tetraalkylammonium hydroxide.

34. The carbonylation catalyst composition of claim 33, wherein the base is tetramethylammonium hydroxide.

35. A carbonylation catalyst composition comprising the following and any reaction products thereof:

an effective amount of palladium(II) 2,4-pentanedionate;

an effective amount of lead(II) oxide;

an effective amount of at least one member selected from the group consisting of titanium(IV) oxide 2,4-pentanedionate, manganese(III) 2,4-pentanedionate, copper(II) 2,4-pentanedionate, and cerium(III) 2,4-pentanedionate; and an effective amount of at least one member selected from the group consisting of sodium acetate, tetrabutylammonium benzoate, tetrabutylammonium sulfate, tetrabutylammonium nitrate, tetrabutylammonium tetraphenylborate, tetraethylammonium para-tolylsulfonate, and tetraethylammonium cyanide;

wherein the carbonylation catalyst composition is free of a halide source.

36. A carbonylation catalyst composition comprising the following and any reaction products thereof:

an effective amount of palladium(II) 2,4-pentanedionate;

an effective amount of lead(II) oxide;

an effective amount of at least one member selected from the group consisting of titanium(IV) oxide 2,4-pentanedionate, manganese(III) 2,4-pentanedionate, copper(II) 2,4-pentanedionate, and cerium(III) 2,4-pentanedionate;

an effective amount of at least one member selected from the group consisting of sodium acetate, tetrabutylammonium benzoate, tetrabutylammonium sulfate, tetrabutylammonium nitrate, tetrabutylammonium tetraphenylborate, tetraethylammonium para-tolylsulfonate, and tetraethylammonium cyanide; and an effective amount of sodium hydroxide;

wherein the carbonylation catalyst composition is free of a halide source.

\* \* \* \* \*